(12) United States Patent
Cucala Escoi et al.

(10) Patent No.: US 7,776,358 B2
(45) Date of Patent: Aug. 17, 2010

(54) EXTENDED RELEASE VENLAFAXINE BESYLATE TABLETS

(75) Inventors: Joan Cucala Escoi, Barcelona (ES); Montserrat Gallego Luengo, Barcelona (ES); Inocencia Margallo Lana, Barcelona (ES)

(73) Assignee: Synthon IP Inc., Gainesville, VA (US)

( * ) Notice: Subject to any disclaimer, the term of this patent is extended or adjusted under 35 U.S.C. 154(b) by 1394 days.

(21) Appl. No.: 10/895,984

(22) Filed: Jul. 22, 2004

(65) Prior Publication Data

US 2006/0018963 A1  Jan. 26, 2006

(51) Int. Cl.
*A61K 9/20* (2006.01)
*A61K 9/24* (2006.01)
*A61K 9/28* (2006.01)
*A61K 9/32* (2006.01)

(52) U.S. Cl. ............... 424/472; 424/464; 424/474; 424/482

(58) Field of Classification Search ............... None
See application file for complete search history.

(56) References Cited

U.S. PATENT DOCUMENTS

| | | | |
|---|---|---|---|
| 4,535,186 A | 8/1985 | Husbands et al. | |
| 5,043,466 A | 8/1991 | Shepard | |
| 5,169,645 A | 12/1992 | Shukla et al. | |
| 5,286,493 A * | 2/1994 | Oshlack et al. | 424/468 |
| 5,916,923 A | 6/1999 | Rudolph et al. | |
| 6,110,498 A * | 8/2000 | Rudnic et al. | 424/473 |
| 6,197,828 B1 | 3/2001 | Jerussi et al. | |
| 6,274,171 B1 | 8/2001 | Sherman et al. | |
| 6,403,120 B1 | 6/2002 | Sherman et al. | |
| 6,419,958 B2 | 7/2002 | Sherman et al. | |
| 6,444,708 B2 | 9/2002 | Rudolph et al. | |
| 6,696,496 B2 | 2/2004 | Oosterbaan et al. | |
| 6,703,044 B1 * | 3/2004 | Pinhasi et al. | 424/452 |
| 6,717,015 B2 * | 4/2004 | Keltjens et al. | 564/355 |
| 2001/0012855 A1 | 8/2001 | Rudolph et al. | |
| 2001/0055612 A1 | 12/2001 | Sherman et al. | |
| 2002/0006443 A1 | 1/2002 | Curatolo et al. | |
| 2003/0190351 A1 | 10/2003 | Platteeuw et al. | |
| 2003/0190353 A1 | 10/2003 | Keltjens et al. | |

FOREIGN PATENT DOCUMENTS

| | | |
|---|---|---|
| EP | 0 797 991 A1 | 10/1997 |
| WO | WO 99/22724 | 5/1999 |
| WO | WO 00/32556 | 6/2000 |
| WO | WO 00/76955 A1 | 12/2000 |

OTHER PUBLICATIONS

Makhija et al., "Once Daily Sustained Release of Venlafxine, a novel antidepressant," Eur. J. Pharm & Biopharm., vol. 54, 2002, pp. 9-15.

* cited by examiner

*Primary Examiner*—Susan Tran
(74) *Attorney, Agent, or Firm*—Muncy, Geissler, Olds & Lowe, PLLC

(57) ABSTRACT

Venlafaxine besylate is formulated into an extended release tablet in high loading rates by use of a coating that contains ammonio methacrylate copolymer(s).

19 Claims, No Drawings

EXTENDED RELEASE VENLAFAXINE BESYLATE TABLETS

BACKGROUND OF THE INVENTION

The present invention relates to a pharmaceutical tablet that provides extended release of venlafaxine besylate.

Venlafaxine, or the compound 1-[2-(dimethylamino)-1-(4-methoxyphenyl)ethyl]-cyclohexanol, is an antidepressant that is sold, as the hydrochloride salt, under the brand name EFFEXOR® (Wyeth Ayerst). The compound is described in U.S. Pat. No. 4,535,186 and a further synthesis thereof is described in U.S. Pat. No. 5,043,466. Venlafaxine hydrochloride is available as an immediate release tablet and as an extended release capsule.

U.S. Pat. No. 6,274,171 and EP 0 797 991 relate to an extended release dosage form of venlafaxine hydrochloride. Specifically, an encapsulated dosage form is taught that comprises spheroids of venlafaxine hydrochloride, microcrystalline cellulose, and hydroxypropylmethylcellulose (HPMC). These spheroids are coated with a mixture of ethyl cellulose and HPMC. By providing an appropriate amount of the coating, the desired blood plasma profile can be obtained. An acceptable batch of coated spheroids meets the following in vitro dissolution profile:

| Time (hours) | Average % venlafaxine hydrochloride released |
|---|---|
| 2 | <30 |
| 4 | 30-55 |
| 8 | 55-80 |
| 12 | 65-90 |
| 24 | >80 |

While the encapsulated dosage form disclosed in these patents appears to be suitable for making an extended release dosage form, the dosage form is somewhat complicated and must be an encapsulated form. A tablet would be desirable. However these patents disclose that "[n]umerous attempts to produce extended release tablets by hydrogel technology proved to be fruitless because the compressed tablets were either physically unstable (poor compressibility or capping problems) or dissolved too rapidly in dissolution studies." See U.S. Pat. No. 6,274,171 at column 4, lines 60-65 and EP 0 797 991A1 at page 3 lines 35-37.

More recently, U.S. Pat. No. 6,717,015 describes venlafaxine besylate as having some advantages over venlafaxine hydrochloride, including lower water solubility. A variety of pharmaceutical compositions are described therein including extended release dosage forms.

It would be desirable to provide additional tablet designs that exhibit extended release of venlafaxine besylate, especially extended release of venlafaxine besylate that is bioequivalent to the commercial venlafaxine hydrochloride extended release capsules.

SUMMARY OF THE INVENTION

The present invention relates to an extended release coated pharmaceutical tablet comprising (a) a tablet core, which comprises at least 70% venlafaxine besylate; and (b) a coating over said tablet core which comprises an ammonio methacrylate copolymer component. The tablet core contains a relatively high amount of venlafaxine besylate, e.g., at least 70% and typically 80-95% venlafaxine besylate. In one embodiment, the tablet core is free of extended release matrix forming excipients. In another embodiment, the tablet core contains a matrix material. The coating typically contains at least 50% of the ammonio methacrylate copolymer component and is generally coated in an amount of 3% to 25% the weight of the tablet core. The invention allows for the formation of relatively small tablets, owing to the high loading of venlafaxine besylate, that exhibit extended release through the application of a simple coating.

DETAILED DESCRIPTION OF THE INVENTION

All percentages refer to weight percent unless otherwise indicated. All coating percentages refer to the dried coating, unless otherwise indicated.

The extended release tablets of the present invention provide a modified, non-immediate release profile of venlafaxine besylate after oral administration. Specifically an "extended release tablet" as used herein means that in a dissolution test using USP Apparatus 2 at 100 rpm and simulated gastric fluid (SGF) or simulated intestinal fluid (SIF), and preferably in each, the tablet releases less than 80%, preferably less than 50%, more preferably less than 30%, of the venlafaxine besylate during the first two hours of the test.

"Venlafaxine besylate" as used herein means any salt formed from venlafaxine and benzene sulfonic acid, including pure or substantially pure (+) or (−) enantiomers, racemic mixtures, crystalline and non-crystalline forms, etc. Venlafaxine besylate and methods of making the same are described in U.S. Pat. No. 6,717,015, which disclosure is incorporated herein by reference. Typically the tablets of the invention contain crystalline venlafaxine besylate monohydrate, such as crystalline (+/−)-venlafaxine besylate monohydrate, (+)-venlafaxine besylate monohydrate, or (−)-venlafaxine besylate monohydrate.

The tablets of the present invention comprise a tablet core and a coating there over. The tablet core comprises at least 70%, typically at least 75%, more typically at least 80% venlafaxine besylate. Venlafaxine besylate is generally relatively easy to compress into tablets and thus does not require a large amount of excipients in order to form a tablettable blend. While technically it is possible to use no excipient, generally some amount of excipient(s) is used. Thus, the amount of venlafaxine besylate in the tablet core is generally not more than 99% and typically not more than 95%. In most embodiments, the amount of venlafaxine besylate is within the range of 75-99%, more typically 80-95%, and in some embodiments 80-90%.

In terms of weight, the tablet core generally contains from 30 to 400 mg of venlafaxine besylate. Typically the amount of venlafaxine besylate is selected to provide a venlafaxine dose amount (i.e., the molar equivalent weight of the venlafaxine free base contained in the venlafaxine besylate) within the range of 30 to 300 mg, typically 37.5 mg, 75 mg, 100 mg, 112.5 mg, 150 mg, 200 mg, or 300 mg.

In addition to the venlafaxine besylate, the tablet core can contain other ingredients, typically pharmaceutically acceptable excipient(s). Pharmaceutically acceptable excipients are well known in the art and include diluents, fillers, binders, lubricants, disintegrants, glidants, colorants, pigments, plasticizers, and any acceptable auxiliary substances such as absorption enhancers, penetration enhancers, surfactants, and co-surfactants. Examples of common types of excipients include various polymers, waxes, calcium phosphates, and sugars. Polymers include cellulose and cellulose derivatives such as HPMC, hydroxypropyl cellulose, hydroxyethyl cellulose, microcrystalline cellulose, carboxymethylcellulose, sodium carboxymethylcellulose, calcium carboxymethylcellulose, and ethylcellulose; polyvinylpyrrolidones; polyethylenoxides; and polyacrylic acids including their copolymers and crosslinked polymers thereof, i.e. Carbopol® (B.F. Goodrich), Eudragit® (Rohm), polycarbophil and chitosan polymers. Waxes include white beeswax, microcrystalline wax, carnauba wax, hydrogenated castor oil, glyceryl behenate, glycerylpalmito stearate, saturated polyglycolyzed glycerate. Calcium phosphates include dibasic calcium phosphate, anhydrous dibasic calcium phosphate, and tribasic calcium phosphate. Sugars include simple sugars such as lactose, maltose, mannitol, fructose, sorbitol, sucrose, xylitol, isomaltose, and glucose as well as complex sugars (polysaccharides) such as maltodextrin, amylodextrin, starches, and modified starches.

Generally the tablet core contains a lubricant in order to accommodate the practicalities of commercial tabletting. The amount of lubricant is generally small, as is conventional in the art, and typically ranges from 0.2 to 2%, more typically 0.5 to 1.5%, of the tablet core. Suitable lubricants include calcium or magnesium soaps, such as magnesium stearate.

In some embodiments, the tablet core also contains a filler. The filler is typically selected from the group consisting of sugars, microcrystalline cellulose, calcium phosphates, and mixtures thereof. The amount of the filler is less than 30%, and typically 5 to 25% of the tablet core. A tablet core can consist of the venlafaxine besylate, the filler(s), and optionally the lubricant, although such is not required and other excipients can be present.

The tablet core may or may not contain an extended release matrix material. In some embodiments the tablet core is free from any such matrix forming material. These kinds of tablets rely on the coating to achieve extended release. However, it is sometimes advantageous to include some amount of a matrix forming agent in the tablet core. Extended release matrix forming agents are well known in the art and include lipophilic matrix materials, hydrophilic matrix materials, inert matrix materials, and biodegradable matrix materials. A lipophilic matrix material is a water-insoluble and non-swellable material that slows the diffusion of the active agent; examples include waxes as described above. A hydrophilic matrix material is generally a polymeric material that swells upon contact with water; examples include hydroxypropylmethylcellulose (HPMC), polysaccharides, polyacrylates, and polyvinyl alcohols. An inert matrix material provides a tortuous pathway and includes ethylcellulose. A biodegradable matrix material includes polyesters of lactic acid and glycolic acid, polyorthoesters, polyanhydrides, and caprolactones. The typical matrix material, if present, is a lipophilic matrix material. The amount of extended release matrix forming material in the tablet core is not greater than 30%, and typically when present is in an amount of 5 to 20%.

The lipophilic matrix material is preferably a fatty acid wax. "Fatty acid wax" as used herein means a material, which is solid at room temperature (i.e. 25° C.), that is made of one or more fatty acids and/or esters of a fatty acid(s) with a mono- and/or polyfunctional alcohol, wherein the preferred alcohol is glycerol. Generally the fatty acids have 12 to 30 carbon atoms, more typically 14 to 24 carbon atoms and the esters generally contain 13 to 80 carbon atoms more typically 18 to 60 carbon atoms. Examples of the fatty acid waxes are palmitic, behenic or stearic acid, glyceryl behenate, glyceryl palmitostearate, hydrogenated castor oil or other natural waxes, including microcrystalline waxes. Accordingly, mixtures of various kinds of fatty acids and fatty acid esters as well as mixtures of waxes all fall under the meaning of "fatty acid wax" in the invention.

While the fatty acid wax can be used to make the tablet core, such as by melt granulation techniques, it is generally considered to be advantageous to co-process the fatty acid wax with a solid filler or flow enhancer to form a modified excipient. Such a modified excipient can be used in a direct compression tabletting technique. The solid filler or flow enhancer include silica, calcium phosphate, and calcium gluconate, but are not limited thereto. The co-processing is not particularly limited and generally is any process that achieves an improvement in the flowability/handling/drug compatibility of the lipophilic matrix material. For example, the flow enhancer can be melt granulated with the wax material to form matrix granules as described in U.S. Pat. No. 5,169,645. Alternatively, the wax material can be coated on and/or combined with the solid filler, especially calcium phosphate, to form particulates. Examples of such a modified excipient made from fatty acid wax and calcium phosphate are described in U.S. application Ser. No. 10/882,669, filed Jul. 2, 2004.

In a preferred embodiment, a co-processed fatty acid wax and calcium phosphate excipient sometimes referred to herein as a "modified calcium phosphate," is used in making the tablet core. The amount of wax in the modified calcium phosphate is not particularly limited and is generally within a calcium phosphate:fatty acid wax weight ratio of 50:50 to 95:5, more typically 60:40 to 85:15, and in some embodiments 70:30 to 80:20 such as about 75:25. Usually the fatty acid wax is glyceryl behenate or glyceryl palmitostearate. Commercially available glyceryl behenate and glyceryl palmitostearate are available as COMPRITOL ATO 888 from Gattefossé and PRECIROL ATO 5 from Gattefossé, respectively. The calcium phosphate is usually dibasic calcium phosphate. Commercially available dibasic calcium phosphate include dihydrate forms such as DI-TAB from Rhodia, DICAFOS from Budenheim, and EMCOMPRESS from Penwest, as well as anhydrous forms such as A-TAB from Rhodia, DICAFOS A/AN from Budenheim, and ANHYDROUS EMCOMPRESS from Penwest. The average particle size of the modified calcium phosphate can be any suitable size for an excipient and typically is within the range from about 50-500 microns, more typically about 125 to 250 microns.

The co-processing of a fatty acid wax and calcium phosphate is generally a coating step. "Coating" is used in its broadest sense of placing the wax on, in, or over the calcium phosphate particles in partial or complete coverage of the particle and specifically includes partial or complete surface coating, void filling, adsorption on and/or impregnating of the calcium phosphate particle. The coating operation, which may comprise one or more steps, results in a particulate composition. Preferably the coating step comprises applying the fatty acid wax in a flowable state to the calcium phosphate. A "flowable state" means that the wax has liquid or liquid-like properties and is generally achieved by heating the wax to at least its softening point, normally about its melting point or higher, or by dissolving or suspending the wax in a solvent to form a solution or slurry, respectively. By applying the wax in a flowable state, coating of the calcium phosphate particles can be carried out by granulation methods including hot melt granulation, melt extrusion, and wet granulation, as well as by spraying and spray-drying methods. Melt granulation is a preferred technique and can be performed as follows.

Powdered or granulated calcium phosphate is mixed with the solid fatty acid wax in desired amounts, e.g., in a weight ratio between 50:50 to 95:5, in suitable mixer equipment. The mixture is heated to a temperature necessary to soften or melt the fatty acid wax in suitable heating equipment such as a high shear granulator or extruder. In general, the recommended temperature of granulating is from 5° C. below the melting point of the wax up to 5° C., more typically 2° C., above the melting point of the wax. In a shear mixer/granulator apparatus, heating the wax mixture above the melting point to form a true liquefied wax can be disadvantageous in that the flowability of the resulting granulate is usually reduced. For example, glyceryl behenate, which has a melting range of 68-72° C., is satisfactorily "melted" by targeting 71° C. Reaching a wax temperature a few degrees higher or lower than 71° C. generally does not adversely affect the resulting granulates. The heating can be performed by a heated jacket, for example, but preferably involves microwave energy. Without wishing to be bound by theory, it is believed that microwave energy heating provides more even heating and heat transfer than simply using external heating such as from a heated jacket and thus avoids or reduces any temperature differential between the sides of the vessel and the center of the vessel. The microwave energy can be the sole heating source or used in combination with other heating sources. Once the wax has been softened and/or melted and sufficiently homogenized with the calcium phosphate particles, an intimate mixture of wax on/within calcium phosphate is provided.

The intimate mixture of calcium phosphate with the wax is then granulated while hot, that is plastic. Conventionally, it is achieved by high speed/sheer mixing the plastic material, using an impeller and a chopper in a granulator, or by extruding the hot mass in an extruder. Advantageously, the step of melting and granulating are performed in the same equipment and it should be noted that all of these operations are advantageously performed in an inert atmosphere such as under vacuum or nitrogen.

The conditions of stirring/chopping depend on the equipment used but they are conventional to a skilled person. The moment of granulate formation may be indicated e.g. by a maximum of torque resistance, e.g. of the impeller in the mixer or the screw in the extruder. The formed granules are then cooled, preferably with gentle mixing, so that also the wax solidifies, and a solid granulated product is the produced.

Aside from the granulation techniques, spraying techniques can be used. For example, a solution or slurry of the fatty acid wax in a solvent can be sprayed onto the calcium phosphate and then dried to form a modified calcium phosphate particulate composition. Similarly, a melted or liquefied fatty acid wax can be sprayed onto the calcium phosphate particles followed by cooling to form a modified calcium phosphate particulate composition. In either case, the calcium phosphate particles are preferably in a gas-operated fluidized bed to facilitate uniform coating of the wax and to encourage a particulate product being formed. In general spraying techniques are less economical when the amount of wax exceeds 15% and can be difficult to operate at wax contents of greater than 25%. Suitable spraying conditions, comparable to known processes wherein an active agent is the coating target such as taught in U.S. Pat. No. 6,194,005 can be used for spraying the calcium phosphate with fatty acid wax to form/maintain a particulate form.

If present, the modified calcium phosphate excipient, which is a combination of a filler and a lipophilic matrix, is generally used in an amount of 5 to 25%, more typically 10 to 20%.

The tablet cores of the present invention can be made by any tabletting technique, including wet granulation, dry granulation, hot melt granulation, or direct compression. Conveniently, direct compression is used to form the tablet core. To facilitate direct compression tabletting, the venlafaxine besylate is typically a crystalline material having a small amount of both fine particles and large particles. Preferably, the venlafaxine besylate contains less than 10% particles having a size under 50 microns and less than 10% particles having a size greater than 500 microns. The average particle size is generally within the range of 50 to 300 microns and typically 75-250 microns. Such a material may be obtained by sieving the solid batch of venlafaxine besylate through sieves of suitable apertures and collecting the fraction having the desired particle size and/or by controlling the crystallization of the material.

The venlafaxine besylate is blended in one or more steps with the other excipients, if any, such as a filler or a modified calcium phosphate and a lubricant to form a homogenous blend and then compressed in a tabletting die to form a tablet. Alternatively, the venlafaxine besylate material is granulated with other excipients such as a lipophilic matrix and the granules, optionally after blending with more excipient(s) such as a lubricant, are compressed into a tablet. The tablets can be any convenient size or shape and typically are within the range of 4 to 12 mm, more typically 4 to 10 mm based on a round tablet. The shapes include round, oval, octagonal, etc. and can be flat or biconvex, but are not limited thereto.

Over the tablet core is a coating that comprises an ammonio methacrylate copolymer component. An "ammonio methacrylate copolymer," as is well known in the art, is characterized as a fully polymerized copolymer of acrylic and methacrylic acid esters with a low content of quaternary ammonium groups. Examples of such copolymers include poly(ethyl acrylate, methyl methacrylate, trimethylammonioethyl methacrylate), although the various alkyl groups could be varied to any C1-C3 alkyl group. The amount of quaternary ammonium group directly relates to the permeability of the polymer coating to water and venlafaxine besylate; higher amounts of ammonium groups provide higher permeability and lower amounts provide for lower permeability. In general the ammonio methacrylate copolymer component contains 7 mol % to 14 mol %, typically 8 mol % to 12 mol %, ammonio methacrylate units. This ratio can be achieved by a single polymer type or species or by a blend of polymer types or species in the ammonio methacrylate copolymer component.

The USP/NF defines ammonio methacrylate copolymers as Type A and Type B, which have approximately 10 mol % ammonio methacrylate groups and approximately 5 mol % ammonio methacrylate groups, respectively. Using the USP/NF definition, some embodiments of the ammonio methacrylate copolymer component comprises 65-100% of Type A ammonio methacrylate copolymer(s) and 35-0% of Type B ammonio methacrylate copolymer(s). More typically, the amounts of Type A and Type B in the ammonio methacrylate copolymer component of the coating are 85-100 and 0-15, respectively. Type A is considered freely water permeable while Type B is considered to be only slightly water permeable. Thus, using a higher amount of Type B ammonio methacrylate copolymer tends to reduce the release rate of the venlafaxine besylate.

Commercially available ammonio methacrylate copolymers include Eudragit® RL series and Eudragit® RS series from Rohm GmbH & Co. KG. The RL copolymer is a Type A and the RS is a Type B. The copolymers are available as an aqueous dispersion/latex and in dissolved form, e.g., as a solution in an organic solvent.

The ammonio methacrylate copolymer component is typically present in an amount of at least 50% and generally 50% to 80% of the coating weight. In addition to the ammonio methacrylate copolymer component, the coating can contain other ingredients including other polymers, plasticizers, glidants, surfactants, etc. Other polymers include acrylic/methacrylic polymers such as the Eudragit NE series as well as ethylcellulose, for example. Normally, the coating also contains 10 to 25% of a plasticizer such as triethyl citrate, and frequently a glidant such as talc. The weight amount of coating, after drying, is usually within 3% to 25%, more typically, 5% to 20%, the weight of the core. The amount depends upon the size of the tablet, the amount of venlafaxine besylate, the content of ammonio methacrylate units, the presence or absence of a matrix material in the tablet core, and the desired release profile. For example, a tablet core that contains a matrix forming material, such as a modified calcium phosphate, will generally need less thick of a coating than the same size and dose tablet made without a matrix material. Further, increasing the amount of Type B ammonio methacrylate copolymer such as Eudragit RS will further restrict the dissolution of the venlafaxine besylate and thus a less thick coating will be sufficient to acquire a reduction in release rate. Further, smaller tablets are generally coated with a higher weight percentage than larger tablets in order to approach the same release profile.

Taking the above into account, for tablet cores that contain 150 mg or more of venlafaxine besylate and/or have a diameter of 7 mm or greater and preferably do not contain a matrix material, the following coating weight and composition can be advantageous: coating in an amount within the range of 5% to 15% of the weight of the tablet core; ammonio methacrylate copolymer component comprises at least 50% of the coating; and the ammonio methacrylate copolymer component comprises 85-100% of a Type A ammonio methacrylate copolymer and 15-0% of a Type B ammonio methacrylate copolymer. Alternatively, for tablet cores that contain less than 150 mg of venlafaxine besylate and/or have a diameter of 7 mm or less and preferably contain a matrix material such as a modified calcium phosphate, the following coating weight and composition can be advantageous: the coating is in an amount within the range of 5% to 25% of the weight of the tablet core; the ammonio methacrylate copolymer component comprises at least 50% of said coating; and the ammonio methacrylate copolymer component comprises 70-100% of a Type A ammonio methacrylate copolymer and 30-0% of a Type B ammonio methacrylate copolymer.

The coating can be formed over the tablet core, optionally with an intermediate processing or coating step in between, by any suitable technique, including spray-, drum-, or pan-coating as are well known in the art. The coating is normally applied as a polymer latex, i.e. an aqueous solution/dispersion.

The extended release tablet of the invention preferably allows for controlled release of the venlafaxine besylate for at least 12 hours, wherein the initial burst is minimized. It is possible to obtain a zero-order or near zero-order release, by selecting the proper core components and the composition and amount of coating.

The venlafaxine containing tablets made according to the present invention preferably meet the following in vitro dissolution profile:

| Time (hours) | Average % venlafaxine released |
|---|---|
| 2 | <30 |
| 4 | 30-55 |
| 8 | 55-80 |
| 12 | 65-90 |
| 24 | >80 | using USP Apparatus 1 (basket) at 100 rpm in purified water at 37° C. Preferably, an extended release dosage form meets the above dissolution profile using a two media dissolution test. Specifically, during the first two hours, the media is a simulated gastric fluid (SGF) of pH 1.2 while during the remaining hours the media is a simulated intestinal fluid (SIF) of pH 6.8. This two media test can provide more accurate predictions of in vivo performance Most advantageously the extended release dosage form meets the above dissolution profile in both 0.1N HCl aqueous solution as well as pure water.

For purposes of the present invention, the simulated fluids are defined as follows: SGF (USP Simulated Gastric Fluid without pepsin) composition:

| | |
|---|---|
| HCl | qs pH 1.2 |
| NaCl | 0.2% |
| water | qs 1000 ml |

SIF (USP Simulated Intestinal Fluid without pancreatin) composition:

| | |
|---|---|
| KH$_2$PO$_4$ | 6.8 g |
| NaOH | qs pH 6.8 |
| water | qs 1000 ml |

In this regard, a preferred tablet is bioequivalent to the commercially available venlafaxine hydrochloride capsule, EFFEXOR XR®.

All of the patents and applications mentioned above are incorporated herein by reference. The invention will be further described with reference to the following non-limiting examples.

EXAMPLE 1

Tablet Composition Comprising Venlafaxine Besylate

Composition of a Tablet Core

| Ingredients | Unit weight | Percentage in the formulation | Description |
|---|---|---|---|
| Venlafaxine besylate monohydrate | 61.30* mg | 85.00% | Active substance |
| Dicalcium phosphate:glyceryl behenate (75/25) | 10.28 mg | 14.25% | Filler |
| Magnesium stearate | 0.54 mg | 0.75% | Lubricant |
| Total weight | 72.12 mg | 100.00% | |

*Equivalent to 37.5 mg venlafaxine as free base

Modus Operandi:
  Manufacturing the Dicalcium Phosphate:Glyceryl Behenate Excipient
Dicalcium phosphate and glyceryl behenate are added to the bowl of a high shear mixer and mixed for 5 minutes. Bowl temperature is increased by hot air and/or microwaves up to approximately 70° C. and a partially melted mass of dicalcium phosphate and glyceryl behenate is obtained. Then, hot air and/or microwaves are stopped and cool water is passed through the jacket and inert gas through the partially melted mass to cool it. This solid product is a free flowing granulate that is sieved to calibrate the size of the granulate.

Compression (Rotary Compression Machine)

Once the filler is obtained, the active is added. This product is mixed for 15 minutes and then magnesium stearate is added and mixed for 5 minutes to obtain a tabletting mixture. This mixture is compressed into round biconvex tablets of 5 mm diameter.

Film Coating (Pan Coating Machine)

These tablets are coated with an ammonio methacrylate copolymer-containing composition.

Film coating formulation to film coat 750-800 g of the previous tablets:

| Ingredients | Weight (g) | Percentage |
|---|---|---|
| Eudragit RL 30 D | 980.00 | Suspension at 30% solids/polymer (294 g) |
| Triethyl citrate | 58.79 | 20% of the solids/polymer quantity |
| Magnesium stearate | 44.09 | 15% of the solids/polymer quantity |
| Simethicone emulsion 30% | 1.47 | 0.07% of the total weight |
| Purified water | 987.94 | Final suspension at 19.15% solids (396.88 g solids/2072.29 g total weight) |
| Total weight | 2072.29 | |

Film Coating Process

| | Inlet air temperature | Tablets temperature | Spray rate | Drum speed |
|---|---|---|---|---|
| Tablets warm-up step | 45° C. | 30-32° C. | — | 4 rpm |
| Film coating step | | | | |
| Up to 2% wt. gain.: | 45° C. | 28-30° C. | 4 g/min | 8 rpm |
| From 2% wt. gain to end of process: | 48-50° C. | 28-30° C. | 8 g/min | 12 rpm |
| Drying step | 45° C. | 30-35° C. | — | 4 rpm |
| Cooling step | 30° C. | 30° C. | — | 4 rpm |

Tablets are cured in trays at 40° C. for 18 hours.

The tablet weight gained is 20%.

Dissolution rate (USP2, 2 hours in SGF pH 1.2 and up to 12 hours in SIF pH=6.8; 37° C.) was determined for venlafaxine besylate by UV spectrophotometry and is expressed in % of the declared amount.

| Hours | % dissolved |
|---|---|
| 0 | 0 |
| 1 | 13.2 |
| 2 | 26.2 |
| 4 | 36.9 |
| 8 | 60 |
| 12 | 78.4 |

EXAMPLE 2

Tablet Composition Comprising Venlafaxine Besylate

Composition of a Tablet Core

| Ingredients | Unit weight | Percentage in the formulation | Description |
|---|---|---|---|
| Venlafaxine besylate monohydrate | 61.30* mg | 85.00% | Active substance |
| Dicalcium phosphate:glyceryl behenate (75/25) | 10.28 mg | 14.25% | Filler |
| Magnesium stearate | 0.54 mg | 0.75% | Lubricant |
| Total weight | 72.12 mg | 100.00% | |

*Equivalent to 37.5 mg venlafaxine as free base

Modus Operandi:
Manufacturing the Dicalcium Phosphate:Glyceryl Behenate Excipient
Same as in Example 1
Compression (Rotary Compression Machine)
Same as in Example 1
Film Coating (Pan Coating Machine)
These tablets are coated with an ammonio methacrylate copolymer-containing composition.
Film Coating Formulation to Film Coat 750-800 g of the Previous Tablets:

| Ingredients | Weight (g) | Percentage |
|---|---|---|
| Eudragit RL 30 D | 343.00 | Suspension at 30% solids/polymer (102.9 g) |
| Eudragit RS 30 D | 147.00 | Suspension at 30% solids/polymer (44.1 g) |
| Triethyl citrate | 29.40 | 20% of the solids/polymer quantity |
| Magnesium stearate | 22.04 | 20% of the solids/polymer quantity |
| Simethicone emulsion 30% | 0.73 | 0.07% of the total weight |
| Purified water | 494.00 | Final suspension at 19.15% solids (198.44 g solids/1036 g total weight) |
| Total weight | 1036.00 | |

Film Coating Process:

The same process as in Example 1 is used for coating the tablets with the formulation.

Tablets are cured in trays at 40° C. for 18 hours.

The tablet weight gained is 10%.

Dissolution rate (USP2, 2 hours in SGF pH 1.2 and up to 24 hours in SIF pH=6.8; 37° C.) was determined for venlafaxine besylate by UV spectrophotometry and is expressed in % of the declared amount.

| Hours | % dissolved |
|---|---|
| 0 | 0 |
| 1 | 11.4 |
| 2 | 24.9 |
| 4 | 40.2 |
| 8 | 67.6 |
| 12 | 86.2 |
| 24 | 106.3 |

EXAMPLE 3

Tablet Composition Comprising Venlafaxine Besylate

Composition of a Tablet

| Ingredient | Unit weight | Percentage in the formulation | Description |
|---|---|---|---|
| Venlafaxine besylate monohydrate | 122.60* mg | 85.00% | Active substance |
| Dicalcium phosphate:glyceryl behenate (75/25) | 20.56 mg | 14.25% | Filler |
| Magnesium stearate | 1.08 mg | 0.75% | Lubricant |
| Total weight | 144.24 mg | 100.00% | |

*Equivalent to 75 mg venlafaxine as free base

Modus Operandi:
Manufacturing the Dicalcium Phosphate:Glyceryl Behenate Excipient
Same as in Example 1
Compression (Rotary Compression Machine)
Once the filler is obtained, the active is added. This product is mixed for 15 minutes and then magnesium stearate is added and mixed for 5 minutes to obtain a tabletting mixture.
This mixture is compressed into round biconvex tablets of 7 mm diameter.
Film Coating (Pan Coating Machine)
These tablets are coated with an ammonio methacrylate copolymer-containing composition.
Film Coating Formulation to Film Coat 750-800 g of the Previous Tablets:

| Ingredients | Weight (g) | Percentage |
|---|---|---|
| Eudragit RL 30 D | 490.00 | Suspension at 30% solids/polymer (147 g) |
| Triethyl citrate | 29.40 | 20% of the solids/polymer quantity |
| Magnesium stearate | 22.04 | 20% of the solids/polymer quantity |
| Simethicone emulsion 30% | 0.73 | 0.07% of the total weight |
| Purified water | 494.00 | Final suspension at 19.15% solid (198.4 g solids/1036 g total weight) |
| Total weight | 1036.00 | |

Film Coating Process:
The same process as in Example 1 is used for coating the tablets with the formulation.
Tablets are cured in trays at 40° C. for 18 hours.
The tablet weight gained is 10%.
Dissolution rate (USP2, 2 hours in SGF pH 1.2 and up to 24 hours in SIF pH=6.8; 37° C.) was determined for venlafaxine besylate by UV spectrophotometry and is expressed in % of the declared amount.

| Hours | % dissolved |
|---|---|
| 0 | 0 |
| 1 | 9.8 |
| 2 | 22.1 |
| 4 | 37.9 |
| 8 | 63.9 |
| 12 | 80.9 |
| 24 | 102 |

EXAMPLE 4

Tablet Composition Comprising Venlafaxine Besylate

Composition of a Tablet

| Ingredients | Unit weight | Percentage in the formulation | Description |
|---|---|---|---|
| Venlafaxine besylate monohydrate | 245.20* mg | 85.00% | Active substance |
| Dicalcium phosphate:glyceryl behenate (75/25) | 41.12 mg | 14.25% | Filler |
| Magnesium stearate | 2.16 mg | 0.75% | Lubricant |
| Total weight | 288.48 mg | 100.00% | |

*Equivalent to 150 mg venlafaxine as free base

Modus Operandi: Manufacturing the Filler, Direct Compression and Film Coating.
Manufacturing the Dicalcium Phosphate:Glyceryl Behenate Excipient
Same as in Example 1
Compression (Rotary Compression Machine)
Once the filler is obtained, the active is added. This product is mixed for 15 minutes and then magnesium stearate is added and mixed for 5 minutes to obtain a tabletting mixture.
This mixture is compressed into round biconvex tablets of 9 mm diameter.
Film Coating (Pan Coating Machine)
These tablets are coated with an ammonio methacrylate copolymer-containing composition.
Film Coating Formulation to Film Coat 750-800 g of the Previous Tablets:

| Ingredients | Weight (g) | Percentage |
|---|---|---|
| Eudragit RL 30 D | 465.50 | Suspension at 30% solids/polymer (139.65 g) |
| Eudragit RS 30 D | 24.50 | Suspension at 30% solids/polymer (7.35 g) |
| Triethyl citrate | 34.75 | 23.6% of the solids/polymer quantity |
| Silicon dioxide (Aerosil 200) | 51.45 | 35% of the solids/polymer quantity |
| Simethicone emulsion 30% | 0.73 | 0.06% of the total weight |
| Purified water | 739.07 | Final suspension at 17.7% solids (233.2 g solids/1316 g total weight) |
| Total weight | 1316.00 | |

Film Coating Process:

The same process as in Example 1 is used for coating the tablets with the formulation.

Tablets are cured in trays at 40° C. for 18 hours.

The tablet weight gained is 4%.

Dissolution rate (USP2, 2 hours in SGF pH 1.2 and up to 12 hours in SIF pH=6.8; 37° C.) was determined for venlafaxine besylate by UV spectrophotometry and is expressed in % of the declared amount.

| Hours | % dissolved |
| --- | --- |
| 0 | 0 |
| 1 | 12.8 |
| 2 | 23.4 |
| 4 | 35.9 |
| 8 | 55.6 |
| 12 | 70 |

EXAMPLE 5

Tablet Composition Comprising Venlafaxine Besylate

Composition of a Tablet

| Ingredient | Unit weight | Percentage in the formulation | Description |
| --- | --- | --- | --- |
| Venlafaxine besylate monohydrate | 245.20* mg | 74% | Active substance |
| Microcrystalline cellulose (Avicel ® PH 102) | 66.27 mg | 20% | Filler |
| Anhydrous dibasic calcium phosphate (A-Tab) | 16.57 mg | 5% | Filler |
| Magnesium stearate | 3.31 mg | 1% | Lubricant |
| Total weight | 331.35 mg | 100% | |

Modus Operandi:

Compression (Rotary Compression Machine)

Venlafaxine besylate, microcrystalline cellulose and anhydrous dibasic calcium phosphate are mixed for 15 minutes and then magnesium stearate is added and mixed for 5 minutes to obtain a tabletting mixture. This mixture is compressed into round biconvex tablets of 9 mm diameter.

Film Coating (Pan Coating Machine)

These tablets are coated with an ammonio methacrylate copolymer-containing composition.

Film Coating Formulation to Film Coat 750-800 g of the Previous Tablets:

| Ingredients | Weight (g) | Percentage |
| --- | --- | --- |
| Eudragit RL 30 D | 490.00 | Suspension at 30% solids/polymer (147 g) |
| Triethyl citrate | 34.75 | 23.6% of the solids/polymer quantity |
| Silicon dioxide (Aerosil 200) | 51.45 | 35% of the solids/polymer quantity |
| Simethicone emulsion 30% | 0.73 | 0.06% of the total weight |
| Purified water | 739.07 | Final suspension at 17.7% solids (233.2 g solids/1316.0 g total weight) |
| Total weight | 1316.00 | |

Film Coating Process:

The same process as in Example 1 is used for coating the tablets with the formulation.

Tablets are cured in trays at 40° C. for 18 hours.

The tablet weight gained is 10%

Dissolution rate (USP2, 2 hours in SGF pH 1.2 and up to 12 hours in SIF pH=6.8; 37° C.) was determined for venlafaxine besylate by UV spectrophotometry and is expressed in % of the declared amount.

| Hours | % dissolved |
| --- | --- |
| 0 | 0 |
| 1 | 13.4 |
| 2 | 23.5 |
| 4 | 32.9 |
| 8 | 50.1 |
| 12 | 63.3 |

EXAMPLE 6

Tablet Composition Comprising Venlafaxine Besylate

Composition of a Tablet

| Ingredient | Unit weight | Percentage in the formulation | Description |
| --- | --- | --- | --- |
| Venlafaxine besylate monohydrate | 245.20* mg | 87.57% | Active substance |
| Lactose (Tablettose ® 80) | 32.70 mg | 11.68% | Filler |
| Magnesium stearate | 2.10 mg | 0.75% | Lubricant |
| Total weight | 280.00 mg | 100.00% | |

Modus Operandi:

Compression (Rotary Compression Machine)

Venlafaxine besylate and lactose are mixed for 15 minutes and then magnesium stearate is added and mixed for 5 minutes to obtain a tabletting mixture. This mixture is compressed into round biconvex tablets of 10 mm diameter.

Film Coating (Pan Coating Machine)

These tablets are coated with an ammonio methacrylate copolymer-containing composition.

Film Coating Formulation to Film Coat 750-800 g of the Previous Tablets:

| Ingredients | Weight (g) | Percentage |
|---|---|---|
| Eudragit RL 30 D | 441.00 | Suspension at 30% solids/polymer (132.3 g) |
| Eudragit RS 30 D | 49.00 | Suspension at 30% solids/polymer (14.7 g) |
| Triethyl citrate | 29.40 | 20% of the solids/polymer quantity |
| Silicon dioxide (Aerosil 200) | 22.04 | 20% of the solids/polymer quantity |
| Simethicone emulsion 30% | 0.73 | 0.07% of the total weight |
| Purified water | 494.00 | Final suspension at 19.15% solids (198.44 g solids/1036.17 g total weight) |
| Total weight | 1036.17 | |

Film Coating Process:
The same process as in Example 1 is used for coating the tablets with the formulation.
Tablets are cured in trays at 40° C. for 18 hours.
The tablet weight gained is 6%.
Dissolution rate (USP2, 2 hours in SGF pH 1.2 and up to 12 hours in SIF pH=6.8; 37° C.) was determined for venlafaxine besylate by UV spectrophotometry and is expressed in % of the declared amount.

| Hours | % dissolved |
|---|---|
| 0 | 0 |
| 1 | 8.8 |
| 2 | 19.1 |
| 4 | 30.7 |
| 8 | 53.8 |
| 12 | 75.6 |

EXAMPLE 7

Tablet Composition Comprising Venlafaxine Besylate

Composition of a Tablet

| Ingredient | Unit weight | Percentage in the formulation | Description |
|---|---|---|---|
| Venlafaxine besylate monohydrate | 61.30* mg | 87.57% | Active substance |
| Lactose (Tablettose ® 80) | 8.18 mg | 11.68% | Filler |
| Magnesium stearate | 0.52 mg | 0.75% | Lubricant |
| Total weight | 70.00 | 100.00% | |

Modus Operandi:
Compression (Rotary Compression Machine)
Venlafaxine besylate and lactose are mixed for 15 minutes and then magnesium stearate is added and mixed for 5 minutes to obtain a tabletting mixture. This mixture is compressed into round biconvex tablets of 5 mm diameter.
Film Coating (Pan Coating Machine)
These tablets are coated with an ammonio methacrylate copolymer-containing composition.

Film Coating Formulation to Film Coat 750-800 g of the Previous Tablets:

| Ingredients | Weight (g) | Percentage |
|---|---|---|
| Eudragit RL 30 D | 441.00 | Suspension at 30% solids/polymer (132.3 g) |
| Eudragit RS 30 D | 49.00 | Suspension at 30% solids/polymer (14.7 g) |
| Triethyl citrate | 29.40 | 20% of the solids/polymer quantity |
| Silicon dioxide (Aerosil 200) | 22.04 | 20% of the solids/polymer quantity |
| Simethicone emulsion 30% | 0.73 | 0.07% of the total weight |
| Purified water | 494.00 | Final suspension at 19.15% solids (198.44 g solids/1036.17 g total weight) |
| Total weight | 1036.17 | |

Film Coating Process:
The same process as in Example 1 is used for coating the tablets with the formulation.
Tablets are cured in trays at 40° C. for 18 hours.
The tablet weight gained is 10%.
Dissolution rate (USP2, 2 hours in SGF pH 1.2 and up to 12 hours in SIF pH=6.8; 37° C.) was determined for venlafaxine besylate by UV spectrophotometry and is expressed in % of the declared amount.

| Hours | % dissolved |
|---|---|
| 0 | 0 |
| 1 | 13.4 |
| 2 | 29.5 |
| 4 | 40.6 |
| 8 | 64.3 |
| 12 | 83.8 |

The invention having been described, it will be readily apparent to those skilled in the art that further changes and modifications in actual implementation of the concepts and embodiments described herein can easily be made or may be learned by practice of the invention, without departing from the spirit and scope of the invention as defined by the following claims.

We claim:

1. An extended release coated pharmaceutical tablet comprising:
   (a) a tablet core, which comprises at least 70% venlafaxine besylate; and
   (b) a coating over said tablet core which comprises an ammonio methacrylate copolymer component, wherein said coating is in an amount within the range of 3% to 25% of the weight of said tablet core.

2. The extended release tablet according to claim 1, wherein said tablet core comprises 75-99% venlafaxine besylate.

3. The extended release tablet according to claim 2, wherein said tablet core contains 80-95% venlafaxine besylate.

4. The extended release tablet according to claim 1, wherein said ammonio methacrylate copolymer component comprises at least 50% of said coating.

5. The extended release tablet according to claim 4, wherein said ammonio methacrylate copolymer component comprises 7 mol % to 14 mol % ammonio methacrylate units.

6. The extended release tablet according to claim 5, wherein said ammonio methacrylate copolymer component comprises 8 mol % to 12 mol % ammonio methacrylate units.

7. The extended release tablet according to claim 4, wherein said ammonio methacrylate copolymer component comprises 65-100% of a Type A ammonio methacrylate copolymer and 35-0% of a Type B ammonio methacrylate copolymer.

8. The extended release tablet according to claim 7, wherein said ammonio methacrylate copolymer component comprises 85-100% of a Type A ammonio methacrylate copolymer and 15-0% of a Type B ammonio methacrylate copolymer.

9. The extended release tablet according to claim 1, wherein said tablet core is free from extended release matrix excipients.

10. The extended release tablet according to claim 9, wherein said tablet core further comprises a lubricant and optionally a filler selected from the group consisting of sugars, microcrystalline cellulose, calcium phosphates, and mixtures thereof.

11. The extended release tablet according to claim 10, wherein said tablet core contains 150 to 300 mg of said venlafaxine besylate.

12. The extended release tablet according to claim 11, wherein said coating is in an amount within the range of 5% to 15% of the weight of said tablet core; said ammonio methacrylate copolymer component comprises at least 50% of said coating; and said ammonio methacrylate copolymer component comprises 85-100% of a Type A ammonio methacrylate copolymer and 15-0% of a Type B ammonio methacrylate copolymer.

13. The extended release tablet according to claim 1, wherein said tablet core further comprises a matrix material.

14. The extended release tablet according to claim 13, wherein said matrix material is a lipophilic matrix material.

15. The extended release tablet according to claim 14, wherein said matrix material is co-processed calcium phosphate and fatty acid wax having a ratio within the range of 85:15 to 65:35, respectively.

16. The extended release tablet according to claim 15, wherein said tablet core comprises 10-20% of said co-processed calcium phosphate and fatty acid wax excipient and 0.2 to 2% of a lubricant.

17. The extended release tablet according to claim 16, wherein said coating is in an amount within the range of 5% to 25% of the weight of said tablet core; said ammonio methacrylate copolymer component comprises at least 50% of said coating; and said ammonio methacrylate copolymer component comprises 70-100% of a Type A ammonio methacrylate copolymer and 30-0% of a Type B ammonio methacrylate copolymer.

18. The extended release tablet according to claim 17, wherein said tablet core comprises 50 to 150 mg of said venlafaxine besylate.

19. The extended release tablet according to claim 1, wherein said tablet exhibits a dissolution profile within the following ranges:

| Time | Venlafaxine |
|---|---|
| 2 hours | <30% |
| 4 hours | 30-55% |
| 8 hours | 55-80% |
| 12 hours | 65-90% |
| 24 hours | >80% | in USP 2 apparatus using SGF, pH 1.2, medium for hours 0-2 and then SIF, pH 6.8, medium for hours 2-24.

* * * * *